United States Patent
Harriman et al.

(10) Patent No.: US 11,566,106 B2
(45) Date of Patent: Jan. 31, 2023

(54) COMPOSITE MATERIALS CONTAINING BENZOXAZINES AND METHOD FOR MAKING THE SAME

(71) Applicant: Cytec Industries Inc., Princeton, NJ (US)

(72) Inventors: Mark Edward Harriman, North Yorkshire (GB); Paul Mark Cross, York (GB); Ram B. Gupta, Stamford, CT (US)

(73) Assignee: Cytec Industries Inc., Princeton, NJ (US)

(*) Notice: Subject to any disclaimer, the term of this patent is extended or adjusted under 35 U.S.C. 154(b) by 0 days.

(21) Appl. No.: 16/891,021

(22) Filed: Jun. 2, 2020

(65) Prior Publication Data
US 2020/0291179 A1 Sep. 17, 2020

Related U.S. Application Data

(62) Division of application No. 14/982,057, filed on Dec. 29, 2015, now abandoned.

(60) Provisional application No. 62/097,280, filed on Dec. 29, 2014.

(51) Int. Cl.
| | |
|---|---|
| *B29C 43/00* | (2006.01) |
| *C08K 5/357* | (2006.01) |
| *C08G 73/02* | (2006.01) |
| *C08J 5/18* | (2006.01) |
| *C08J 5/24* | (2006.01) |
| *C08L 61/34* | (2006.01) |
| *C08G 14/06* | (2006.01) |
| *C07D 265/16* | (2006.01) |
| *C08J 5/04* | (2006.01) |
| *B29C 39/00* | (2006.01) |

(52) U.S. Cl.
CPC ........ *C08G 73/0233* (2013.01); *B29C 39/003* (2013.01); *B29C 43/003* (2013.01); *C07D 265/16* (2013.01); *C08G 14/06* (2013.01); *C08J 5/04* (2013.01); *C08J 5/18* (2013.01); *C08J 5/24* (2013.01); *C08K 5/357* (2013.01); *C08L 61/34* (2013.01); *C08J 2361/34* (2013.01)

(58) Field of Classification Search
CPC ... B29C 39/003; B29C 45/0005; C08G 73/02; C08G 73/0233; C08L 61/34; C08K 5/357; C07D 265/14
See application file for complete search history.

(56) References Cited

U.S. PATENT DOCUMENTS

| | | | | |
|---|---|---|---|---|
| 6,160,079 A * | 12/2000 | Ishida | .................. | C07D 265/16 528/129 |
| 2010/0140542 A1* | 6/2010 | Ji | ......................... | C07D 265/16 252/182.23 |
| 2010/0204400 A1* | 8/2010 | Kreiling | ............. | C08G 59/4014 524/590 |
| 2013/0267659 A1* | 10/2013 | Ward | ..................... | C08L 61/34 524/611 |

* cited by examiner

*Primary Examiner* — Karuna P Reddy
(74) *Attorney, Agent, or Firm* — Thi Dang

(57) ABSTRACT

A curable composition containing more than 80% by weight of a blend of benzoxazines, wherein the blend includes (A) one or more multifunctional benzoxazines and (B) a liquid, non-halogenated monofunctional benzoxazine. This composition has been found to be stable at high temperatures, e.g. 180° C.-250° C., and suitable for making composite materials using conventional techniques such as prepregging and liquid resin infusion.

6 Claims, 2 Drawing Sheets

COMPOSITE MATERIALS CONTAINING BENZOXAZINES AND METHOD FOR MAKING THE SAME

The instant application is a divisional application of U.S. application Ser. No. 14/982,057 filed on Dec. 29, 2015, which claims the benefit of U.S. Provisional Patent Application No. 62/097,280 filed on Dec. 29, 2014, both prior filed applications are incorporated by reference in their entirety.

Benzoxazines offer a number of advantages as compared to other thermosetting resins including relatively long shelf-life, molecular design flexibility, low cost, high glass transition temperature ($T_g$), high modulus, relatively low viscosities, good flame retardant properties (due to a high phenolic and tertiary amine content), low moisture absorption, no by-products released during curing and very low shrinkage upon curing. Furthermore, benzoxazines are capable of being self-cured upon heating; i.e. there is no need for an additional curing agent. This combination of properties means that benzoxazines are potentially attractive for use in aerospace applications. In particular they may be useful as the thermosetting matrix in composite materials. However, currently available multifunctional benzoxazines are glassy solids at room temperatures making them difficult to process using standard techniques such as prepregging for the fabrication of fiber-reinforced resin composites, such as those used for aerospace applications.

"Prepregging" refers to the process of impregnating unidirectionally aligned reinforcing fibers or woven fabric with a resin matrix to form prepregs in the form of tapes or sheets. These prepregs are then laid up onto each other in a particular orientation on a tool to form a laminate. The prepreg lay-up is then subjected to elevated temperature and pressure to cure and consolidate the composite part. The method of pressure application is dependent on the part and configuration, but the use of an autoclave is most common for high-performance structural parts.

Resin infusion approach differs from that of conventional prepregging in that dry structural reinforcement fibers are placed into a mold cavity or other shaping tool, and a matrix resin is injected or infused into the structural reinforcement fibers. Resin infusion covers processing techniques such as Resin Transfer Molding (RTM), Liquid Resin Infusion (LRI), Resin Infusion under Flexible Tooling (RIFT), Vacuum Assisted Resin Transfer Molding (VARTM), Resin Film Infusion (RFI) and the like. Such conventional techniques require the resins to be of relatively low viscosity and to be thermally stable at processing temperatures.

DETAILED DESCRIPTION

Figure 1:
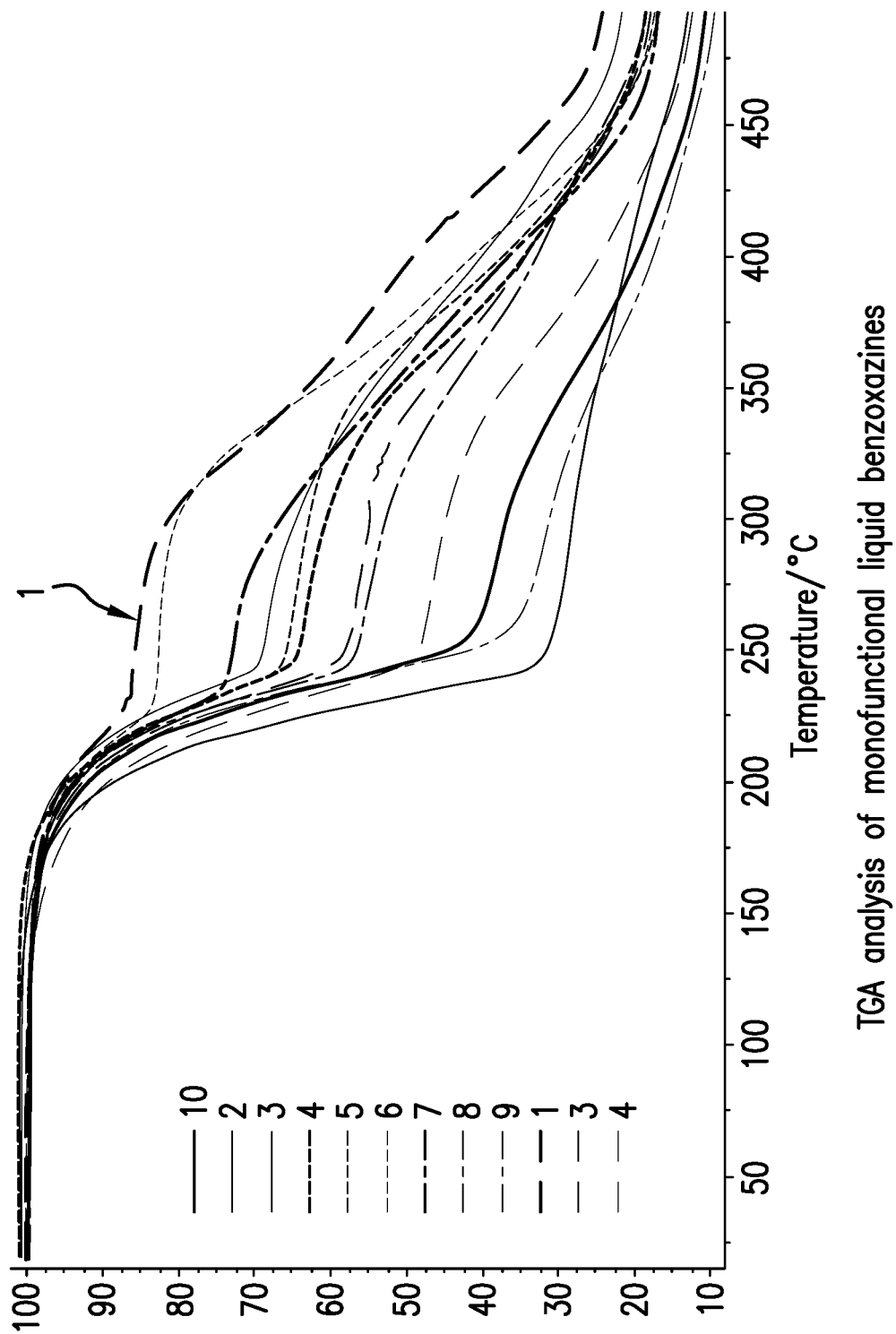
FIG. 1 shows Thermogravimetric Analysis (TGA) of various monofunctional liquid benzoxazines for comparison.

Neat benzoxazine resins based on multifunctional benzoxazines are very glass-like at room temperature (20° C.-30° C.), meaning that they also have very poor processability characteristics. Liquid monofunctional benzoxazines can lower uncured resin $T_g$ to room temperature (20° C.-30° C.) or lower, allowing enhanced processability by conventional prepregging processes. Some liquid monofunctional benzoxazines are commercially available, e.g. Huntsman's RDB 2009-008, but they are limited in application as they suffer from being unstable at temperatures normally used in cure cycles for the manufacture of aerospace composite structures (180° C. or higher). Several benzoxazine hybrid formulations based on epoxy-benzoxazine blends are commercially available (Henkel Loctite BZ 9703, BZ 9704, BZ 9705.2), but the addition of the epoxy as a co-reactant negates some of the benefits brought on by neat benzoxazines, such as modulus and the cured dry-wet $T_g$ differential.

Neat benzoxazine resins based on multifunctional benzoxazines are very viscous in their melt state meaning that they also have very poor resin infusion processability characteristics. Liquid monofunctional benzoxazines can decrease viscosity at typical infusion temperatures, allowing enhanced processability. Some liquid monofunctional benzoxazines are commercially available, e.g. Huntsman's RDB 2009-008, but they are limited in application as they suffer from being very unstable at temperatures normally used in cure cycles for the manufacture of aerospace composite structures (180° C. or higher), potentially causing issues with voiding. Several benzoxazine hybrid formulations based on epoxy-benzoxazine blends are commercially available (Henkel Loctite BZ 9110, BZ 9120, BZ 9130), but the addition of the epoxy as a co-reactant negates some of the benefits brought on by neat benzoxazines, such as modulus and the cured dry-wet $T_g$ differential.

To address the issues relating to process-ability of benzoxazine resins, a benzoxazine-based composition containing a blend of one or more multifunctional benzoxazines having functionality of 2 or greater and a liquid, non-halogenated monofunctional benzoxazine is disclosed herein. The blend of benzoxazines is making up for more than 80% by weight of the curable composition. According to one embodiment, the benzoxazine-based composition can be formulated to have an uncured $T_g$ of 15° C. to 22° C., viscosity below 2 Pa·s at about 30° C. and be stable at high temperatures within the range of 180° C.-250° C. In another embodiment, the composition is formulated to have an uncured $T_g$ of 20° C. to 30° C. for the purpose of fabricating prepreg therefrom. The uncured $T_g$ as discussed herein is measured by Differential Scanning calorimetry (DSC). In yet another embodiment, the composition is formulated to have a viscosity of less than 5 Pa·s at injection temperature for resin infusion, for example, in the range of about 100° C. to about 150° C.

As used herein, "monofunctional benzoxazine" refers to a compound which does not have more than one benzoxazine unit, or a compound which is substantially a reaction product of monohydric phenol and monofunctional amine, and "multifunctional benzoxazine" refers to a compound having more than one benzoxazine unit. The benzoxazine unit being referred herein includes an oxazine ring pendant to a benzene ring).

Non-Halogenated Monofunctional Benzoxazine

The non-halogenated, monofunctional benzoxazine compound of the present disclosure is represented by the following Structure 1:

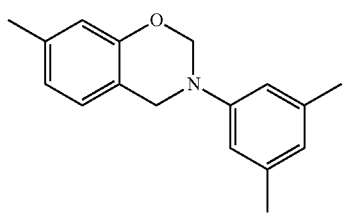
(1)

It has been discovered that other monofunctional benzoxazine compounds having similar structures (Structures 2-10 below) are unstable at the same temperature range. This shows the unpredictable nature of monofunctional benzoxazine compounds.

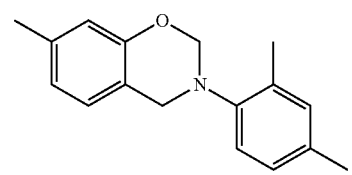
2

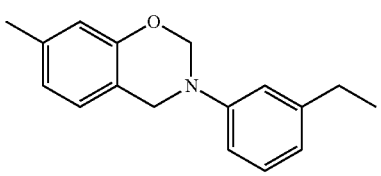
3

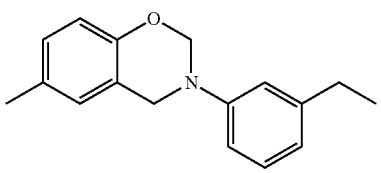
4

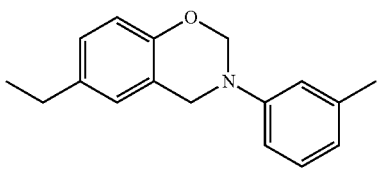
5

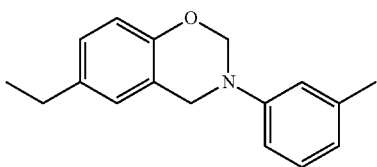
6

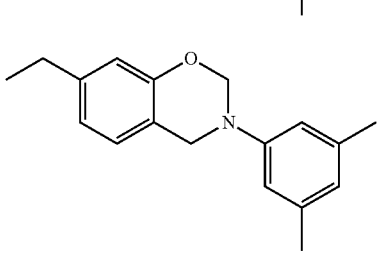
7

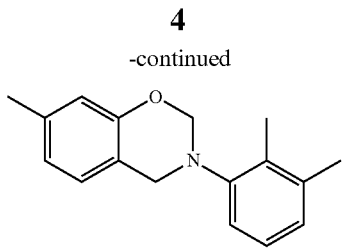
8

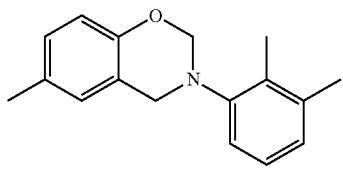
9

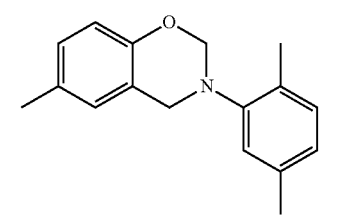
10

The non-halogenated, monofunctional benzoxazine compound of Structure 1 is in liquid form at temperature between 20° C.-30° C., particularly, 20° C.-25° C. and has a viscosity of 5 Pa·s at about 30° C. It remains in its liquid state for a long period of time, at least 4 years. Moreover, it is thermally stable at temperatures within the range of 180° C.-250° C. "Thermally stable" means that the benzoxazine does not decompose, i.e. liberate volatile species either during or after cure in the temperature range of up to 250° C., and shows weight loss of less than 15% at this temperature range as determined by Thermogravimetric Analysis (TGA). FIG. 1 shows the TGA analysis of the monofunctional benzoxazine compounds of Structures 1-10 for comparison.

In one embodiment, the non-halogenated monofunctional benzoxazine could be synthesized by reacting m-cresol, aromatic amine, and paraformaldehyde. The reaction is depicted below with 3,5-xylidine as the representative aromatic amine.

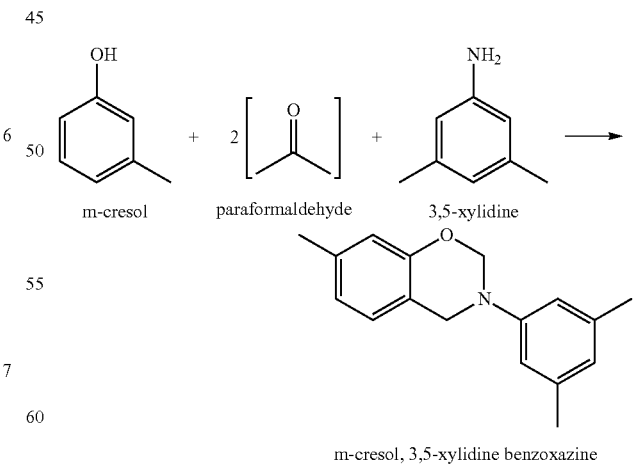

m-cresol, 3,5-xylidine benzoxazine

The stoichiometry for m-cresol, paraformaldehyde, and aromatic amine is 1:2:1 molar ratio.

The temperature stability discussed above is unusual for non-halogenated, liquid benzoxazines. While not wanting to be bound by any theory, it is believed that this temperature stability is due to the favouring of a specific reaction site on the molecule by judicious choice of substituents on the aniline.

The liquid, monofunctional benzoxazine of the present disclosure may be blended with difunctional and/or trifunctional benzoxazines to improve the process-ability of these multifunctional benzoxazines, which are normally solid at room temperature. The presence of liquid monofunctional benzoxazine improves the process-ability of the benzoxazine-based resin composition by reducing the viscosity and reducing $T_g$ of the uncured composition, making it suitable for resin-film impregnation of reinforcement fibers to form prepregs by lowering the uncured $T_g$ and/or suitable for liquid resin infusion of dry fibrous preform, e.g., via RTM, by lowering the viscosity.

Difunctional Benzoxazines

The difunctional benzoxazines that are suitable for the purposes herein include those represented by the following Formula I:

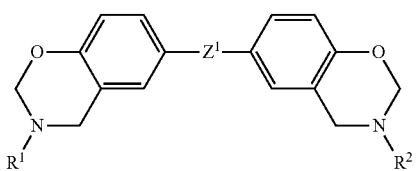

where $Z^1$ is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings of the benzoxazine moieties may be fused; and $R^1$ and $R^2$ are independently selected from alkyl (preferably $C_{1-8}$ alkyl), cycloalkyl (preferably $C_{5-7}$ cycloalkyl, preferably $C_6$ cycloalkyl) and aryl, wherein the cycloalkyl and aryl groups are optionally substituted, for instance by $C_{1-8}$ alkyl, halogen and amine groups, and preferably by $C_{1-8}$ alkyl, and where substituted, one or more substituent groups (preferably one substituent group) may be present on each cycloalkyl and aryl group;

in one embodiment, $Z^1$ is selected from a direct bond, —C($R^3$)($R^4$)—, —C($R^3$)(aryl)-, —C(O)—, —S—, —O—, a divalent heterocycle and —[C($R^3$)($R^4$)]$_x$-arylene-[C($R^5$)($R^6$)]$_y$—, or the two benzyl rings of the benzoxazine moieties may be fused;

$R^3$, $R^4$, $R^5$ and $R^6$ are independently selected from H, $C_{1-8}$ alkyl (preferably $C_{1-4}$ alkyl, and preferably methyl), and halogenated alkyl (wherein the halogen is typically chlorine or fluorine (preferably fluorine) and wherein the halogenated alkyl is preferably $CF_3$); and x and y are independently 0 or 1;

where $Z^1$ is selected from a divalent heterocycle, it is preferably 3, 3-isobenzofuran-1(3h)-one, i.e. wherein the compound of formula (I) is derived from phenolphthalein;

where $Z^1$ is selected from —[C($R^3$)($R^4$)]$_x$-arylene-[C($R^5$)($R^6$)]$_y$—, then the chain linking the two benzoxazine groups may further comprise one or more arylene group(s) and/or one or more —C($R^7$)($R^8$)— group(s) where $R^7$ and $R^8$ are independently selected from the groups defined hereinabove for $R^3$.

In a preferred embodiment, the arylene group is phenylene. In one embodiment, the groups attached to the phenylene group may be configured in para- or meta-positions relative to each other. In a preferred embodiment, the aryl group is phenyl.

The group $Z^1$ may be linear or non-linear, and is typically linear. The group $Z^1$ is preferably bound to the benzyl group of each of the benzoxazine moieties at the para-position relative to the oxygen atom of the benzoxazine moieties, as shown in formula (I), and this is the preferred isomeric configuration. However, the group $Z^1$ may also be attached at either of the meta-positions or the ortho-position, in one or both of the benzyl group(s) in the bis-benzoxazine compound. Thus, the group $Z^1$ may be attached to the benzyl rings in a para/para; para/meta; para/ortho, meta/meta or ortho/meta configuration. In one embodiment, the difunctional benzoxazine resin component comprises a mixture of isomers, preferably wherein the major portion of the mixture is the para/para isomer shown in Formula I and preferably this is present in at least 75 mol %, preferably at least 90 mol %, and preferably at least 99 mol %, of the total isomeric mixture.

In a preferred embodiment, the difunctional benzoxazine is selected from compounds wherein $Z^1$ is selected from —C(CH$_3$)$_2$—, —CH$_2$— and 3,3-isobenzofuran-1(3H)-one, i.e. benzoxazine derivatives of bisphenol A, bisphenol F and phenolphthalein.

In another embodiment, the difunctional benzoxazine is selected from compounds wherein $R^1$ and $R^2$ are independently selected from aryl, preferably phenyl. In one embodiment, the aryl group may be substituted, preferably wherein the substituent(s) are selected from $C_{1-8}$ alkyl, and preferably wherein there is a single substituent present on at least one aryl group. $C_{1-8}$ alkyl includes linear and branched alkyl chains. Preferably, $R^1$ and $R^2$ are independently selected from unsubstituted aryl, preferably unsubstituted phenyl.

The benzyl ring in each benzoxazine group of the difunctional benzoxazine compounds defined herein may be independently substituted at any of the three available positions of each ring, and typically any optional substituent is present at the position ortho to the position of attachment of the $Z^1$ group. Preferably, however, the benzyl ring remains unsubstituted.

An alternative Formula II for the difunctional benzoxazines is represented below:

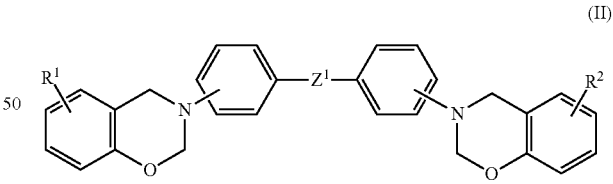

wherein is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings may be fused; and $R^1$ and $R^2$ are independently selected from hydrogen, alkyl (preferably $C_{1-8}$ alkyl), cycloalkyl (preferably $C_{5-7}$ cycloalkyl, preferably $C_6$ cycloalkyl) and aryl, wherein the cycloalkyl and aryl groups are optionally substituted, for instance by $C_{1-8}$ alkyl, halogen and amine groups, and preferably by $C_{1-8}$ alkyl, and where substituted, one or more substituent groups (preferably one substituent group) may be present on each cycloalkyl and aryl group; in one embodiment, $Z^1$ is selected from a direct bond, —C($R^3$)($R^4$)—, —C($R^3$)(aryl)-, —C(O)—, —S—, —O—, a divalent heterocycle and —[C($R^3$)($R^4$)]$_x$-arylene-[C($R^5$)($R^6$)]$_y$—, or the two benzyl rings may be fused;

$R^3$, $R^4$, $R^5$ and $R^6$ are independently selected from H, $C_{1-8}$ alkyl (preferably $C_{1-4}$ alkyl, and preferably methyl), and halogenated alkyl (wherein the halogen is typically chlorine or fluorine (preferably fluorine) and wherein the halogenated alkyl is preferably $CF_3$); and x and y are independently 0 or 1;

where $Z^1$ is selected from a divalent heterocycle, it is preferably 3, 3-isobenzofuran-1(3h)-one, i.e. wherein the compound of formula (II) is derived from phenolphthalein;

where $Z^1$ is selected from —[C($R^3$)($R^4$)]$_x$-arylene-[C($R^5$)($R^6$)]$_y$—, then the chain linking the two benzoxazine groups may further comprise one or more arylene group(s) and/or one or more —C($R^7$)($R^8$)— group(s) where $R^7$ and $R^8$ are independently selected from the groups defined hereinabove for $R^3$, provided that the or each substituted or unsubstituted methylene group is not adjacent to another substituted or unsubstituted methylene group.

In a preferred embodiment, the arylene group is phenylene. In one embodiment, the groups attached to the phenylene group may be configured in para- or meta-positions relative to each other. In a preferred embodiment, the aryl group is phenyl.

The group $Z^1$ may be linear or non-linear, and is typically linear. The group $Z^1$ may be attached at the meta-positions, the para-positions or the ortho-position, in one or both of the benzyl group(s) in the bis-benzoxazine compound. Thus, the group $Z^1$ may be attached to the benzyl rings in a para/para; para/meta; para/ortho, meta/meta or ortho/meta configuration. In one embodiment, the thermoset benzoxazine resin component (A) comprises a mixture of isomers, preferably wherein the major portion of the mixture is the para/para isomer shown in structure IV, and preferably this is present in at least 75 mol %, preferably at least 90 mol %, and preferably at least 99 mol %, of the total isomeric mixture.

In a preferred embodiment, the di-functional benzoxazine is selected from compounds wherein $Z^1$ is selected from —C($CH_3$)$_2$—, —$CH_2$— and 3,3-isobenzofuran-1(3H)-one In another embodiment, the difunctional benzoxazine is selected from compounds wherein $R^1$ and $R^2$ are independently selected from aryl, preferably phenyl. In one embodiment, the aryl group may be substituted, preferably wherein the substituent(s) are selected from $C_{1-8}$ alkyl, and preferably wherein there is a single substituent present on at least one aryl group. $C_{1-8}$ alkyl includes linear and branched alkyl chains. Preferably, $R^1$ and $R^2$ are independently selected from unsubstituted aryl, preferably unsubstituted phenyl.

The benzyl ring in the di-functional benzoxazine compounds defined herein may be independently substituted at any of the three available positions of each ring, and typically any optional substituent is present at the position ortho to the position of attachment of the $Z^1$ group. Preferably, however, the benzyl ring remains unsubstituted.

Specific examples of suitable di-functional benzoxazines include:

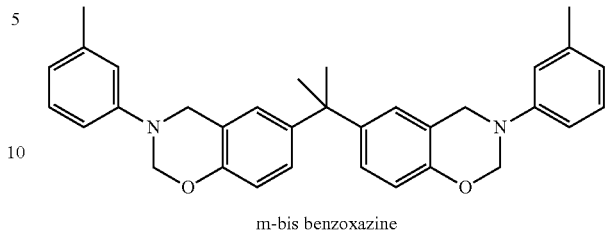

m-bis benzoxazine

In a preferred embodiment, the di-functional benzoxazine is meta-substituted difunctional (or bis-) benzoxazine or di-meta-substituted difunctional benzoxazine.

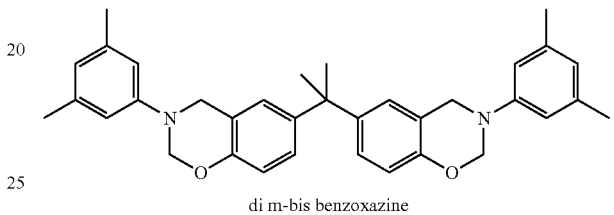

di m-bis benzoxazine

Tri-Functional Benzoxazines

Suitable tri-functional benzoxazines include compounds derived from reacting aromatic triamines with monohydric or polyhydric phenols in the presence of formaldehyde or alkyl formcel. Specific examples of suitable trifunctional benzoxazines include:

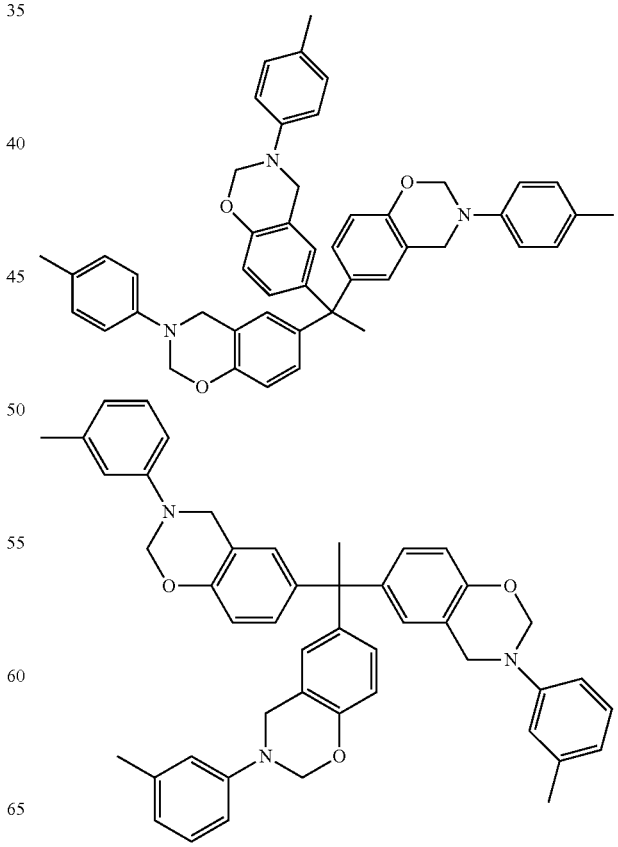

-continued

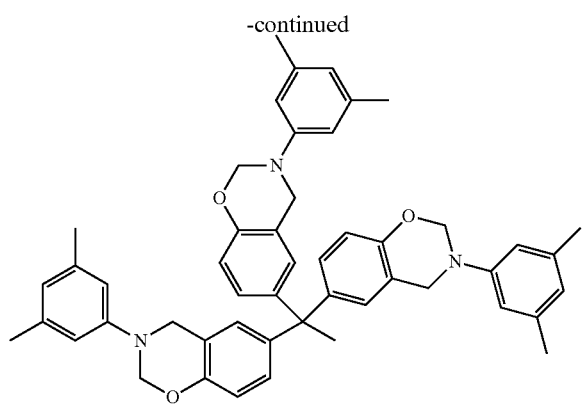

Curable Compositions

The non-halogenated monofunctional benzoxazine compound of Structure 1 may be combined with one or more multifunctional benzoxazine compounds to form a blend. Curable compositions may be formulated such that the benzoxazine blend constitutes more than 80% by weight, preferably, at least 85% by weight of the total weight of the composition. The curable compositions containing the benzoxazines disclosed herein are formulated to remain thermally stable (i.e., not degraded) at temperatures equal to or above 180° C., e.g. 180° C.-250° C.

According to one embodiment, a curable composition is formulated to contain more than 80% by weight, preferably, at least 85% by weight of a benzoxazine blend, which contains the non-halogenated monofunctional benzoxazine compound of Structure land at least one di-functional benzoxazine. The weight ratio of monofunctional benzoxazine to difunctional benzoxazine may be from 40:60 to 10:90, in some cases, 50:50 to 10:90.

According to another embodiment, the curable composition contains more than 80% by weight, preferably, at least 85% by weight of a benzoxazine blend, which contains the liquid benzoxazine compound of Structure 1 and at least one trifunctional benzoxazine compound, wherein the mass ratio of liquid benzoxazine to trifunctional benzoxazine is from about 50:50 to about 10:90.

According to yet another embodiment, the curable composition contains more than 80% by weight, preferably, at least 85% by weight of a benzoxazine blend, which contains the liquid benzoxazine compound of Structure 1, at least one di-functional benzoxazine, and at least one tri-functional benzoxazine, wherein the trifunctional benzoxazine is at maximum 25% by weight based on the total weight of the benzoxazine blend. According to yet another embodiment, a curable composition is formulated to contain the non-halogenated monofunctional benzoxazine compound of Structure 1, at least one di-functional benzoxazine, specifically m-substituted bis-benzoxazine, and at least one tri-functional benzoxazine, specifically m-substituted tris-benzoxazine. It is preferred that the combination of monofunctional and difunctional benzoxazine is at a minimum of 85% by weight based on the total weight of the benzoxazine blend, and the trifunctional benzoxazine is at maximum 15% by weight based on the total weight of the benzoxazine blend.

The curable compositions discussed above may further include additional components, such as tougheners and catalysts, but the total amount of all benzoxazines in the composition is equal to or greater than 80% by mass.

Unlike many conventional benzoxazine-based compositions, the benzoxazine-based composition of the present disclosure does not require the presence of a solvent. Although it is possible to add a minor amount of solvent to further enhance film-formation.

For prepregging, the $T_g$ of the curable composition may be adjusted by the appropriate proportions of monofunctional and multifunctional benzoxazines to enable the formation of continuous resin films, which are subsequently used to impregnate reinforcement fibers.

For resin infusion, the viscosity of the curable composition may be adjusted by the appropriate proportions of monofunctional and multifunctional benzoxazines to a maximum of 5 Pa·s and a preferred viscosity of 1 Pa·s or less at processing temperature, for example, within the range of 100° C.-150° C.

As used herein, a "curable composition" refers to a composition prior to curing. Upon curing, the monofunctional and multifunctional benzoxazines readily polymerize via ring opening polymerization. Such polymerization may be initiated cationically (using cationic initiators) or thermally.

The addition of catalysts/accelerators is optional, but the use of such additives may increase the cure rate and/or reduce the cure temperatures. Suitable catalysts/accelerators for the benzoxazine-based resin composition include, but are not limited to, Lewis acids, such as phenols and derivatives thereof, strong acids, such as alkylenic acids, methyl tosylate, cyanate esters, p-toluenesulfonic acid, 2-ethyl-4-methylimidazole (EMI), 2,4-di-tert-butylphenol, $BF_3O(Et)_2$, adipic acid, organic acids, phosphorous pentachloride ($PCl_5$).

Toughening agents (or tougheners) may be added to produce a toughened resin matrix suitable for manufacturing advanced composite structures. Suitable toughening agents include, but are not limited to, thermoplastic toughening agents such as polyethersulphone (PES), co-polymer of PES and polyetherethersulphone (PEES), elastomers, including liquid rubbers having reactive groups, particulate toughening agents such as thermoplastic particles, glass beads, rubber particles, and core-shell rubber particles.

Functional additives may also be included to influence one or more of mechanical, rheological, electrical, optical, chemical, flame resistance and/or thermal properties of the cured or uncured resin composition. Examples of such functional additives include, but are not limited to, fillers, color pigments, rheology control agents, tackifiers, conductive additives, flame retardants, ultraviolet (UV) protectors, and the like. These additives may take the form of various geometries including, but are not limited to, particles, flakes, rods, and the like.

Composite Materials

To form composite materials, the reinforcing fibers are impregnated or infused with the curable resin composition using conventional processing techniques such as prepregging and resin infusion. After resin impregnation or infusion, curing is carried out at elevated temperature up to 250° C., preferably in the range of 160° C. to 220° C., more preferably at about 180° C.-200° C., and with the use of elevated pressure to restrain deforming effects of escaping gases, or to restrain void formation, suitably at pressure of up to 10 bar, preferably in the range of 3 to 7 bar abs. Suitably the cure temperature is attained by heating at up to 5° C./min. for example 2° C. to 3° C./min and is maintained for the required period of up to 9 hours, preferably up to 6 hours, for example 3 to 4 hours. Temperature may be reduced by cooling at up to 5° C./min. for example up to 3° C./min. Post-curing at temperatures in the range of 190° C. to 250°

C. may be performed, at atmospheric pressure, employing suitable heating rates to improve the glass transition temperature of the product or otherwise.

To fabricate prepregs, a resin film may be formed from the curable resin composition by, for example, roll-coating, extrusion, compression moulding, extrusion, melt-casting or belt-casting, followed by laminating such film to one or both opposing surfaces of a layer of reinforcement fibers in the form of, for example, a non-woven mat of relatively short fibers, a woven fabric of continuous fibers, or a layer of unilaterally aligned fibers (i.e., fibers aligned along the same direction), at temperature and pressure sufficient to cause the resin film to soften and impregnate the fibers. Alternatively, the prepreg may be fabricated by providing the curable resin composition in liquid form, and passing the layer of fibers through the liquid resin composition to infuse the layer of fibers with the heat curable composition, and removing the excess resin from the infused fibrous layer.

To fabricate a composite part from prepregs, plies of impregnated reinforcing fibers are laid up on a tool and laminated together by heat and pressure, for example by autoclave, vacuum or compression moulding, or by heated rollers, at a temperature above the curing temperature of the resin composition.

The resulting multi-ply layup may be anisotropic in which the fibres are continuous and unidirectional, orientated essentially parallel to one another, or quasi-isotropic in which the fibres in a ply are orientated at an angle, e.g. 45°, 30°, 60° or 90°, relative to those in the plies above and below. Orientations intermediate between anisotropic and quasi-isotropic, and combination thereof, may also be provided. Woven fabrics are an example of quasi-isotropic or intermediate between anisotropic and quasi-isotropic. Suitable layup contains at least 4, preferably at least 8 plies. The number of plies is dependent on the application for the layup, for example, the strength required, and layups containing 32 or even more, for example several hundred, plies may be desirable to form large composite parts. There may be provided toughening interleaf or toughening particles, in the interlaminar regions between plies.

To fabricate a composite part through resin infusion, e.g. RTM or VaRTM processes, the first step is to form a dry fiber preform in the shape of the desired structural part. The preform generally includes a number of fabric layers or plies made from dry reinforcement fibers that impart the desired reinforcing properties to a resulting composite part. Nonwoven veils, for example, nonwoven thermoplastic veils composed of randomly oriented thermoplastic fibers, may be interleaved between adjacent fabric plies as toughening materials. After the fiber preform has been formed, the preform is placed in a mold. The curable resin composition is injected/infused directly into fiber preform, and then the resin-infused preform is cured.

The reinforcement fibers for forming composite materials and parts may take the form of whiskers, short fibers, continuous fibers, filaments, tows, bundles, sheets, plies, and combinations thereof. Continuous fibers may further adopt any of unidirectional, multi-directional, non-woven, woven, knitted, stitched, wound, and braided configurations, as well as swirl mat, felt mat, and chopped-fiber mat structures. The composition of the fibers may be varied to achieve the required properties for the final composite structure. Exemplary fiber materials may include, but are not limited to, glass, carbon, graphite, aramid, quartz, polyethylene, polyester, poly-p-phenylene-benzobisoxazole (PBO), boron, polyamide, graphite, silicon carbide, silicon nitride, and combinations thereof.

EXAMPLES

Example 1

The following synthesis was used for the reaction of m-cresol, 3,5-xylidine and paraformaldehyde to form a substantially monofunctional benzoxazine:

1. 18.68 g m-cresol, 20.94 g 3,5-xylidine and 20.76 g paraformaldehyde were added to a 250 ml glass jar.
2. The mixture was then mixed at room temperature (~20.0° C.) for 20 minutes.
3. The jar was immersed in an oil bath, the temperature of the oil bath was increased to 115° C., and the mixture was stirred for a further 40 minutes. A colour change occurred at this stage.

| Sandy brown/cream | | Orange/Brown |
|---|---|---|
| Opaque | → | Transparent |
| Low Viscosity | | Low Viscosity |

4. The oil bath was increased in temperature to 120° C. (took approximately 2 minutes to reach temperature) and the mixture was mixed for a further 20 minutes.
5. The glass jar was removed from the oil bath and allowed to cool for approximately 5 minutes. The reaction product containing benzoxazine was then slowly added to 10 ml diethyl ether whilst stirring. This mixture was then stirred for a further 20 minutes at room temperature (~20.0° C.).
6. Once stirred, the resulting benzoxazine-ether mixture was washed 3 times with 2.0M NaOH solution in water, in 100 ml portions, in a separating funnel.
7. A further water wash was carried out to neutralise the pH (pH7) after the addition of the NaOH.
8. This mixture was left overnight and then magnesium sulphate drying agent added to mixture and dried for 4 hours.
9. Residual ether was removed on a rotary evaporated under vacuum for 15 minutes at 50° C.
10. The final product was dried under vacuum at 60° C. in a vacuum oven for 2 hours, resulting in a non-halogenated liquid benzoxazine (labeled as "L-BOX") containing m-cresol, 3,5-xylidine benzoxazine as a major component.

Rheological analysis at 30° C. shows that the viscosity of the non-halogenated liquid benzoxazine was 5 Pa·s.

A resin blend containing meta-Bisphenol-A benzoxazine and the non-halogenated liquid benzoxazine L-BOX was prepared as follows (meta-Bisphenol A benzoxazine 70:30 liquid benzoxazine, in mass ratio).

1. 12.0 g of liquid benzoxazine and 28.0 g of meta-Bisphenol-A benzoxazine were degassed separately in a vacuum oven at 110° C. for 90 minutes.
2. 9.0 g of the degassed liquid benzoxazine and 21.0 g of the degassed meta-Bisphenol-A benzoxazine were added to a 250 ml glass jar.
3. The blend of materials was immersed in an oil bath at 90° C. for 30 minutes and then stirred at 90° C. for 45 minutes.
4. The blend was removed from the oil bath and poured into aluminum dishes.
5. The dishes of blended benzoxazine were degassed in a vacuum oven at 110° C. for 90 minutes.

The degassed benzoxazine blends were cured using the following cure cycle: 25° C. to 180° C. at 1° C. min$^{-1}$, held for 2 hr, 180° C. to 200° C. at 1° C. min$^{-1}$, held for 2 hr, 200° C. to 25° C. at 2° C. min$^{-1}$.

The lower viscosity of the non-halogenated monofunctional benzoxazine provided significant improvement in processing of a 70:30 meta-Bisphenol-A benzoxazine to monofunctional benzoxazine formulation relative to neat meta-Bisphenol-A benzoxazine. This has been observed in both resin filming for prepregging and also when the films were applied to a carbon fabric. Resin filming was carried out using a conventional knife over plate coating tool onto a silicon based release paper.

Resin films were produced using the benzoxazine resin blend discussed above. The resin films showed no signs of resin loss from the release paper during the filming process. Some tack was observed at room temperature and the resin film could be folded and bent with none of the resin breaking away from the release paper.

This compared favourably to when neat bisphenol-A benzoxazine was filmed under the same conditions. With bisphenol-A benzoxazine the film was lost from the silicon treated release paper under roll-up of the film. This means that any prepreg manufactured from the film would be of poor and inconsistent quality.

Example 2

The following four monofunctional benzoxazines were prepared by reacting phenol, paraformaldehyde and an amine selected from aniline, o-toluidine, m-toluidine, and p-toluidine.

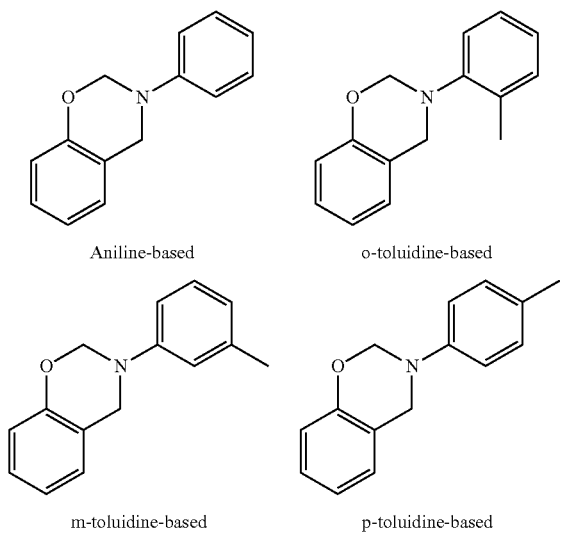

Aniline-based    o-toluidine-based m-toluidine-based    p-toluidine-based

The physical state of the synthesized benzoxazines at room temperature (~25° C.) was found as follows:

| | |
|---|---|
| 1.) Aniline-based | Liquid with some solid particles appearing on the side of the glass jar after one month. |
| 2.) o-toluidine-based | Liquid |
| 3.) m-toluidine-based | Liquid but solidified after 7.5 weeks. |
| 4.) p-toluidine-based | Liquid but solidified after drying in vacuum oven during preparation. |

Figure 2:
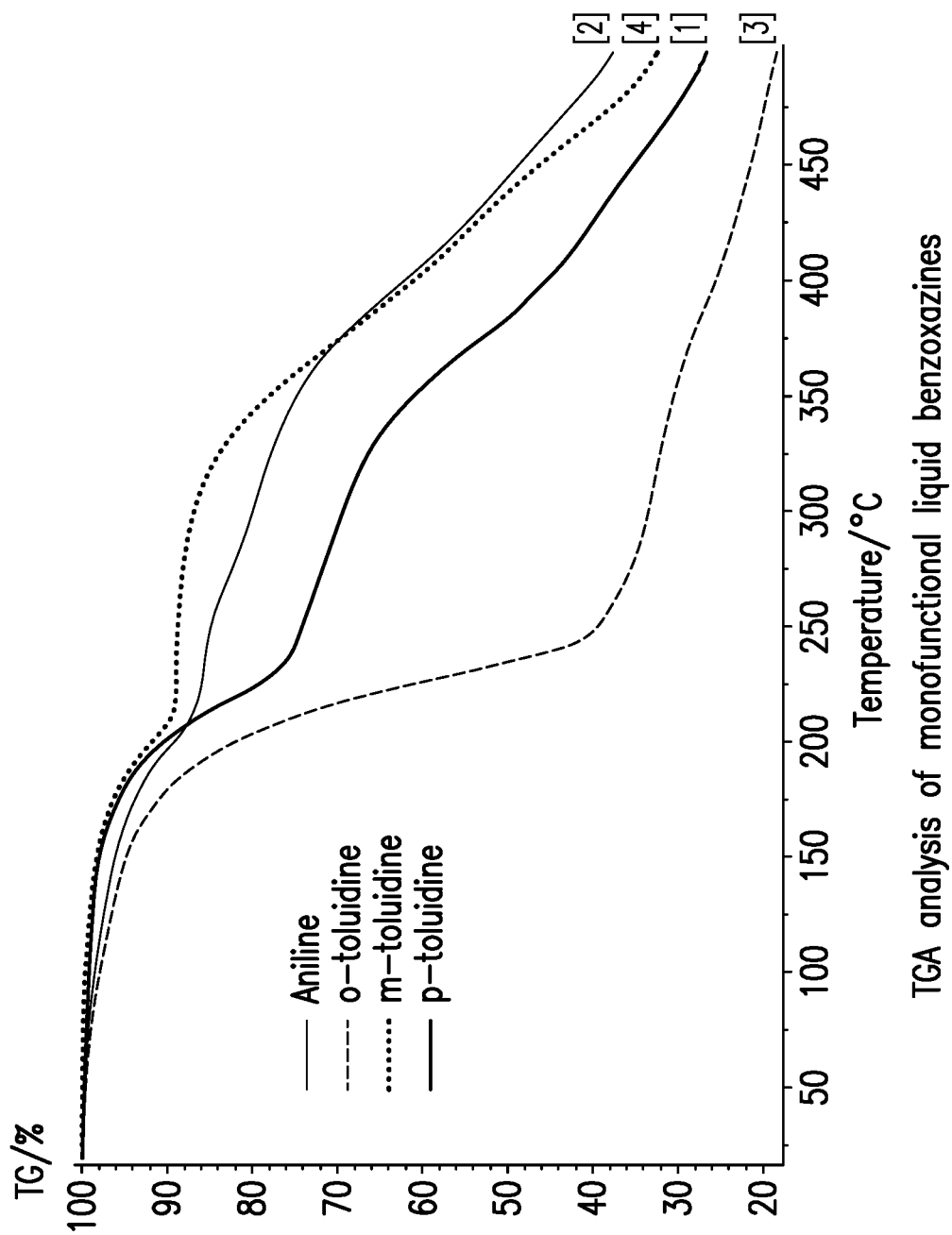
FIG. 2 shows TGA of monofunctional benzoxazines derived from using different amines: aniline, o-toluidine, m-toluidine, and p-toluidine.

FIG. 2 shows the TGA analysis of these benzoxazines. P-toluidine-based and o-toluidine-based benzoxazines were not stable in the temperature range of 180° C. to 250° C.

Blends of Bisphenol-A benzoxazines and each of the synthesized monofunctional benzoxazines were prepared according to the weight ratio of 30:70 monofunctional benzoxazine to bisphenol-A benzoxazine. A 30:70 blend of the liquid monofunctional benzoxazine L-BOX prepared in Example 1 and bisphenol-A benzoxazine was also prepared. The resin samples were then cured according to the following curing cycle: heating to 180° C. at 1° C./min, held for 2 hr, 180° C. to 200° C. at 1° C./min, held for 2 hr. The $T_g$ of the cured resin samples were measured by a Dynamic Mechanical Analysis (DMA) method and are reported in Table 1.

TABLE 1

| Monofunctional benzoxazine (30) | Bis-A benzoxazine (70) | $T_g$ (° C.) |
|---|---|---|
| L-BOX | | 187 |
| Aniline-based | | 161 |
| o-toluidine-based | | 153 |
| m-toluidine-based | | 174 |
| p-toluidine-based | | 159 |

As can be seen from Table 1, cured $T_g$ of the resin sample containing L-BOX is higher than that of other resin samples. This means that L-BOX can be utilized at higher temperatures after curing. Also, it was found that p-toluidine-based and o-toluidine-based benzoxazines were not stable during cure cycle, and showed weight loss of more than 15% at this temperature range as determined by TGA. As such, they are not suitable for forming prepregs and composite structures.

Ranges disclosed herein are inclusive and independently combinable, and is inclusive of the endpoints and all intermediate values within the ranges. For example, the range of "1% to 10%" includes 1%, 2%, 3%, 4%, 5%, 6%, 7%, 8%, 9%, 10% as well as intermediate values such as 1.1%, 1.2%, 1.3%, etc.

While various embodiments are described herein, it will be appreciated from the specification that various combinations of elements, variations of embodiments disclosed herein may be made by those skilled in the art, and are within the scope of the present disclosure. In addition, many modifications may be made to adapt a particular situation or material to the teachings of the embodiments disclosed herein without departing from essential scope thereof. Therefore, it is intended that the claimed invention not be limited to the particular embodiments disclosed herein, but that the claimed invention will include all embodiments falling within the scope of the appended claims.

What is claimed is:

1. A method for forming a prepreg comprising:
   (i) forming a continuous resin film from a curable composition comprising more than 80% by mass of a benzoxazine blend; and
   (ii) pressing the continuous resin film onto a layer of reinforcement fibers with application of heat so as to impregnate the layer of reinforcement fibers,
   wherein said benzoxazine blend consists of:
   (A) a non-halogenated, monofunctional benzoxazine compound that is in liquid form at a temperature in the range of 20° C.-30° C. and has the following structure:

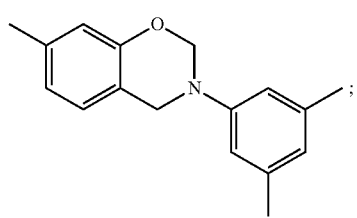

and (B) a multifunctional benzoxazine component comprising at least one trifunctional benzoxazine compound selected from the group consisting of following compounds:

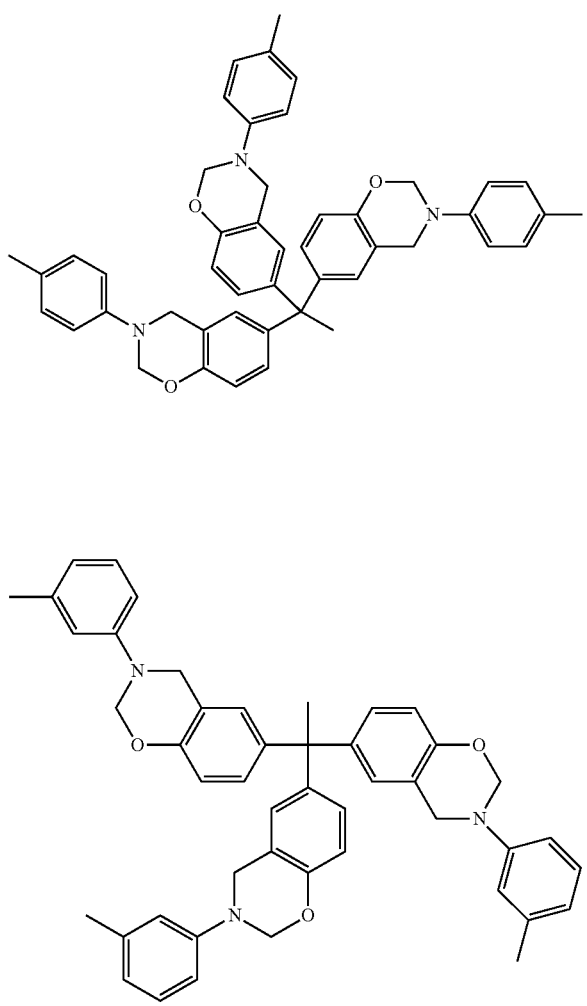

and

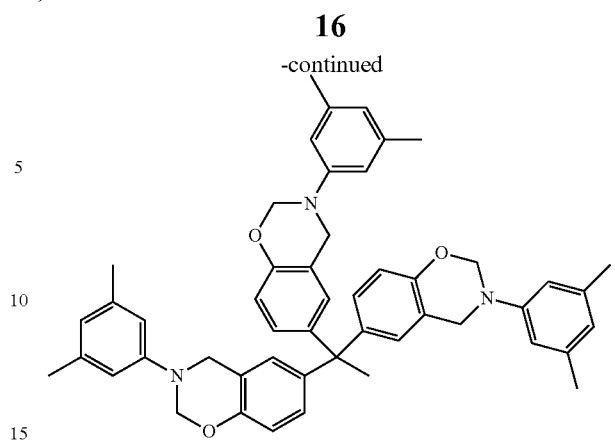

wherein the mass ratio of (A) to (B) is from 50:50 to 10:90, and wherein the curable composition exhibits an uncured $T_g$ of 30° C. or lower as measured by Differential Scanning calorimetry (DSC).

2. The method of claim 1, wherein the layer of reinforcement fibers is in the form of unidirectional fibers, a woven fabric or a non-woven mat.

3. The method of claim 1, wherein the multifunctional benzoxazine component (B) further comprises a di-functional benzoxazine selected from the following compounds:

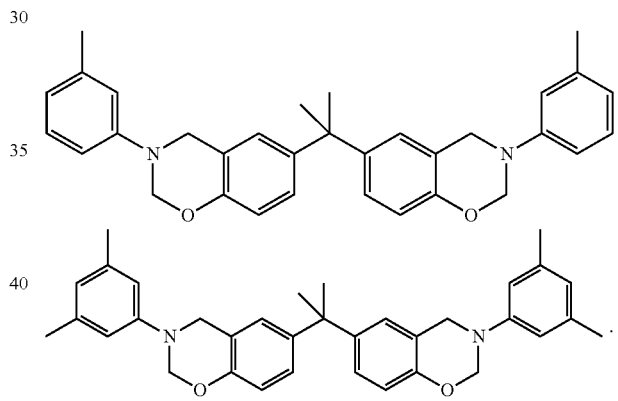

4. The method of claim 1, wherein the curable composition is void of or contains less than 5% by weight, based on the total weight of the composition, of any thermosettable resin selected from epoxy, cyanate ester, bismaleimide, and phenol-formaldehyde.

5. The method of claim 1, wherein the curable composition is void of any organic solvent.

6. The method of claim 1, wherein the layer of reinforcement fibers comprises fibers selected from carbon fibers, glass fibers, aramid fibers, and combinations thereof.

* * * * *